(12) United States Patent
Kojian

(10) Patent No.: US 11,975,021 B1
(45) Date of Patent: May 7, 2024

(54) TOPICAL COMPOSITIONS COMPRISING EMULSIFIED POVIDONE IODINE SOLUTIONS AND METHODS OF PREPARATION

(71) Applicant: James Kojian, Arcadia, CA (US)

(72) Inventor: James Kojian, Arcadia, CA (US)

(*) Notice: Subject to any disclaimer, the term of this patent is extended or adjusted under 35 U.S.C. 154(b) by 0 days.

(21) Appl. No.: 18/378,069

(22) Filed: Oct. 9, 2023

(51) Int. Cl.
| | |
|---|---|
| A61K 33/18 | (2006.01) |
| A61K 9/06 | (2006.01) |
| A61K 31/138 | (2006.01) |
| A61K 31/167 | (2006.01) |
| A61K 31/573 | (2006.01) |
| A61K 47/26 | (2006.01) |
| A61K 47/44 | (2017.01) |

(52) U.S. Cl.
CPC ............ *A61K 33/18* (2013.01); *A61K 9/06* (2013.01); *A61K 31/138* (2013.01); *A61K 31/167* (2013.01); *A61K 31/573* (2013.01); *A61K 47/26* (2013.01); *A61K 47/44* (2013.01)

(58) Field of Classification Search
CPC ........ A61K 33/18; A61K 9/06; A61K 31/138; A61K 31/167; A61K 31/573; A61K 47/26; A61K 47/44
See application file for complete search history.

(56) References Cited

U.S. PATENT DOCUMENTS

| | | | | |
|---|---|---|---|---|
| 2001/0012851 A1* | 8/2001 | Lundy | ............... | A61K 45/06 |
| | | | | 548/510 |
| 2008/0260655 A1* | 10/2008 | Tamarkin | ............ | A61P 35/00 |
| | | | | 424/45 |
| 2017/0087199 A1* | 3/2017 | Patron | ............ | A61K 31/381 |

FOREIGN PATENT DOCUMENTS

WO    WO-2023023580 A1 *   2/2023

OTHER PUBLICATIONS

JP2001163783A machine translation (Year: 2001).*

* cited by examiner

*Primary Examiner* — Robert A Wax
*Assistant Examiner* — Quanglong N Truong
(74) *Attorney, Agent, or Firm* — Italia IP; James A. Italia

(57) ABSTRACT

Compositions for treating inflammatory skin conditions are described. The compositions can include povidone iodine in aqueous solution, hydrocortisone, diphenhydramine, an emulsifier, and a hydrophobic carrier, where the povidone iodine aqueous solution is emulsified in the hydrophobic carrier. A method of preparing a composition is also described. The method can include adding an aqueous solution of povidone iodine to a hydrophobic carrier, and adding an emulsifier to the hydrophobic carrier at a concentration that emulsifies the aqueous solution of povidone iodine in the hydrophobic carrier upon mixing.

18 Claims, 10 Drawing Sheets

(9 of 10 Drawing Sheet(s) Filed in Color)

|  | Polysorbate 80, NF | Sorbitan Monooleate (Span 80) | Polysorbate 20 NF |
|---|---|---|---|
| Total weight added |  |  |  |
| Weight of Starting ointment | 7.03 grams | 7.03 grams | 7.03 grams |
| Emulsifier Drops |  |  |  |
| Baseline Description |  |  |  |
| Weight (0.1ml) | 0.11 g | 0.1g | 0.11g |
| Description (picture) | 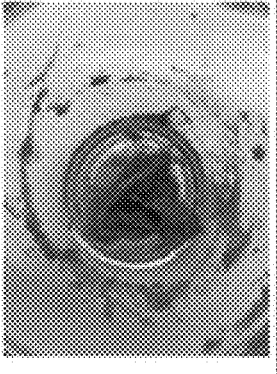 | 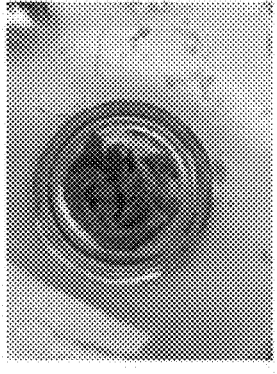 |  |
| Weight added (0.1ml) | 0.22 g | 0.2 g | 0.22 g |
| Description | Smoother but still chunky | Smoother and easier to manipulate*** | Getting harder faster than polysorbate 80 at this step. |
FIG. 2

| | Polysorbate 80, NF | Sorbitan Monooleate (Span 80) | Polysorbate 20 NF |
|---|---|---|---|
| Weight added (0.1ml) Description | 0.33 g Not sticking to glass as much*** | 0.3 g Thicker (soften caramel-like) consistency). Friction while trying to blend | 0.33 g Very Sticker, not easy to move in the bowl. Lots of friction |
| Total Weight added (0.4ml) Description | 0.44 g Getting sticky and harder to mix. Stick chunky | 0.4 g Smoother but stickier | 0.44 g Color change, still mixable |

FIG. 3

| | Polysorbate 80, NF | Sorbitan Monooleate (Span 80) | Polysorbate 20 NF |
|---|---|---|---|
| ? | | 0.7 g | |
| Description | | About the same as last time but the compound is darker than last time. | |
| Final Weight | 6.62 g | 5.93 g | 6.69 g |

FIG. 5

| Date Made | Name | Ingredients | Concentration | Calculated weight to add (grams) | Actual Weight added (grams) | Image and time picture was taken after compounding |
|---|---|---|---|---|---|---|
| 9/1/23 | 10% Betadine in petrolatum | Betadine | 10% | 3 | 3.01 | 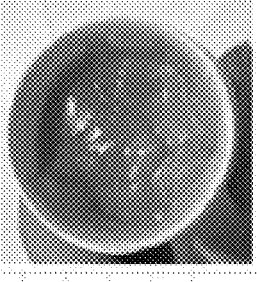 5 days later |
| | | Poly 80 | 8% | 2.4 | 2.41 | |
| | | Hydrocortisone | 1% | 0.3 | 0.312 | |
| | | Diphenhydramine | 2% | 0.6 | 0.609 | |
| | | Petrolatum (Base) | | 23.7 | 23.760 | |
| | | Total Weight | 30g | | | |
| 9/1/23 | 15% Betadine in petrolatum | Betadine % | 15% | 4.5 | 4.52 | 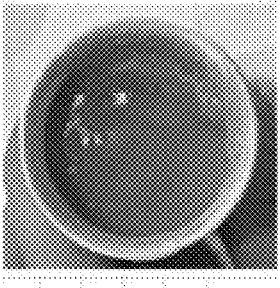 5 days later |
| | | Poly 80 | 8% | 2.4 | 2.42 | |
| | | Hydrocortisone | 1% | 0.3 | 0.30 | |
| | | Diphenhydramine | 2% | 0.6 | 0.605 | |
| | | Petrolatum (Base) | | 22.2 | 22.23 | |
| | | Total Weight | 30g | | | |
| 9/1/23 | 20% Betadine in petrolatum | Betadine | 20% | 6 | 6.002 | 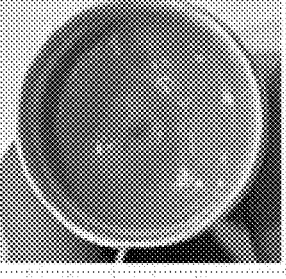 5 days later |
| | | Poly 80 | 8% | 2.4 | 2.407 | |
| | | Hydrocortisone | 1% | 0.3 | 0.301 | |
| | | Diphenhydramine | 2% | 0.6 | 0.608 | |
| | | Petrolatum (Base) | | 20.7 | 20.72 | |
| | | Total Weight | 30 | | | |

TOPICAL COMPOSITIONS COMPRISING EMULSIFIED POVIDONE IODINE SOLUTIONS AND METHODS OF PREPARATION

FIELD

The present disclosure is directed to the field of pharmaceuticals. More particularly, the present disclosure is directed to topical compositions for treating inflammatory skin conditions, and methods of preparing such compositions.

SUMMARY

In general, in a first aspect, the disclosure features a composition. The composition can include povidone iodine aqueous solution, hydrocortisone, diphenhydramine, an emulsifier, and a hydrophobic carrier, where the povidone iodine aqueous solution is emulsified in the hydrophobic carrier.

In general, in a second aspect, the disclosure features a method of preparing a composition. The method can include adding povidone iodine aqueous solution to a hydrophobic carrier, and adding an emulsifier to the hydrophobic carrier at a concentration that emulsifies the aqueous solution of povidone iodine in the hydrophobic carrier upon mixing.

Features of the method and composition can include the following. The composition can further include lidocaine. The emulsifier can be polysorbate 80. The hydrophobic carrier can be a cream, lotion, or ointment. The hydrophobic carrier can include one or more ingredients chosen from petrolatum, mineral oil, and a wax. Povidone iodine aqueous solution can be present in the composition at a concentration of 0.1% to 20% (w/w), or greater. Hydrocortisone can be present in the composition at a concentration of 0.1% to 1.0% (w/w), or greater. Diphenhydramine can present in the composition at a concentration of 0.1% to 2% (w/w), or greater. Polysorbate 80 can be present in the composition at a concentration of 0.1% to 8.0% (w/w), or greater. Lidocaine can be present in the composition at a concentration of 0.1% to 4.0% (w/w), or greater. The hydrophobic carrier can include petrolatum or can be an anhydrous ointment base including mineral oil, white petrolatum, and emulsifying wax which is capable of preparing water-in-oil emulsions.

It should be understood that the methods and compositions are not to be considered limitations on the invention defined by the claims. The featured methods and compositions can be implemented in one or more ways using one or more features depicted in the drawings, described in the detailed description, and set forth in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate certain aspects and principles of the implementations set forth, and should not be construed as limiting.

FIGS. 2-5 are tables showing the results of ointment formulation experiments of a 20% BETADINE® ointment in MEDISCA® Emulsifying Base testing three different emulsifiers (polysorbate 80, sorbitan monooleate, polysorbate 20).

FIGS. 8 and 9 are tables showing summaries of ointment formulation experiments using different concentrations (10%, 15%, 20% w/w) of BETADINE® in petrolatum (FIG. 8), and 20% w/w BETADINE® in different bases (emulsifying base, 50% emulsifying base/50% petrolatum, 25% emulsifying base/75% petrolatum, FIG. 9).

FIG. 10A is a formula sheet showing an example ointment formulation ingredient list. The ingredient list is for an ointment having 20% w/w BETADINE®, 2% w/w diphenhydramine HCL, 1% w/w hydrocortisone, and 8% w/w polysorbate 80, compounded in a MEDISCA® Emulsifying Ointment Base.

FIG. 10B is an image providing instructions for compounding the ingredients listed in FIG. 10A.

DETAILED DESCRIPTION

Reference will now be made in detail to various illustrative implementations. It is to be understood that the following discussion of the implementations is not intended to be limiting.

The disclosure pertains to compositions for treating insect bites and other dermal conditions involving inflammatory responses. The composition can be implemented as anti-itch cream, lotion, or ointment that includes BETADINE® aqueous solution (or the active pharmaceutical ingredient (API) povidone iodine), diphenhydramine HCL, hydrocortisone, and optionally, lidocaine, formulated in a hydrophobic carrier or vehicle. The hydrophobic carrier can be a cream or lotion including carrier oils or a petroleum-derived ointment. The composition can be applied topically to relieve various ailments involving dermal immune responses, including reducing itch from various dermal issues including bug bites, athlete's foot (tinea pedis), contact dermatitis (eczema), and reaction to poisonous plants such as poison ivy. These are just a sample of therapeutic applications and many more will be discussed herein.

The compositions are engineered to treat the various pharmacological and biochemical pathways involved in the immune response to a bug bite or other dermal condition, including histamine response, inflammatory response, antigen foreign protein response and sensory response. The specific pharmacological agents in the composition neutralize the complex physiological pathways central to these responses and as such provide a highly efficacious treatment for individuals suffering from these skin conditions.

The present inventor has circumvented the difficulty in incorporating aqueous solutions of povidone iodine, which is water soluble or hydrophilic, into oleaginous ointment carriers, which are hydrophobic. After extensive trial and error, the present inventor has discovered that certain concentrations of polysorbate will facilitate mixing the aqueous povidone iodine solution in a hydrophobic carrier such as an emulsifying base and create a stable ointment holding the liquid as well as all of the other different ingredients of the composition. The present inventor has determined the proper amounts of polysorbate, oleaginous ointment base and aqueous povidone iodine solution, diphenhydramine HCL, hydrocortisone, and optionally, lidocaine that provide an ointment that is stable, absorbable through the skin, and effective in stopping the itch in less than 10 minutes and eradicating the insect bite sequela or other dermal condition.

Figure 1A:
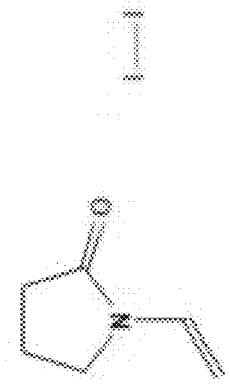
FIGS. 1A-E are chemical structures for povidone iodine (FIG. 1A), polysorbate 80 (FIG. 1B), hydrocortisone (FIG. 1C), diphenhydramine HCL (FIG. 1D), lidocaine (FIG. 1E).

The composition can incorporate or include the following ingredients:

Povidone iodine is a water-soluble complex of iodine and polyvinylpyrrolidone having a molecular weight of 364.95 g/mol. On a dry basis, it contains from 9.0% to 12.0% available iodine. Its physical appearance is that of a yellowish-brown amorphous hygroscopic powder. The complex has broad anti-microbial activity through liberation of free iodine which iodinates components of eukaryotic and prokaryotic cell membrane such as lipids, killing or neutralizing bacteria, fungi, protozoa, and viruses. Povidone iodine is used as a topical antiseptic to prepare for surgery, and for treating skin infections. Names for povidone iodine formulations include BETADINE® (Atlantis Consumer Healthcare Inc., Bridgewater, NJ, USA), Isodine, Bridine, and Disphex. Povidone iodine has IUPAC name 1-ethenylpyrrolidin-2-one; molecular iodine and CAS Registry No. 25655-41-8. BETADINE® is formulated as 10% povidone-iodine aqueous solution, and also formulated as an antiseptic spray (povidone-iodine, 5%, in solution or dry power) or as a surgical scrub (7.5% povidone-iodine aqueous solution). The chemical structure of povidone iodine is provided in FIG. 1A.

Figure 1B:
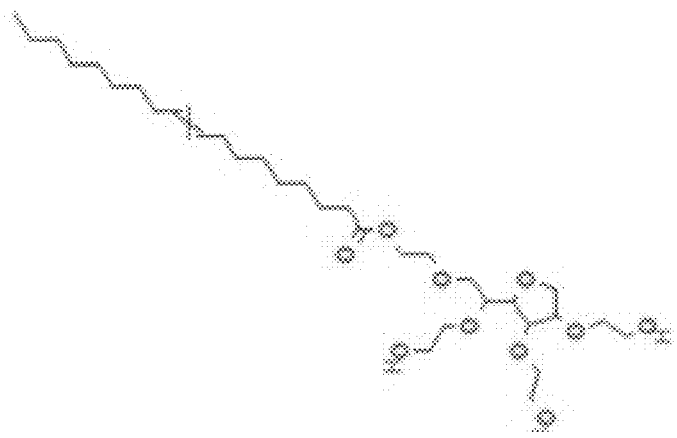

Polysorbate (e.g., polysorbate 80) is a hydrophilic non-ionic surfactant formed by reacting sorbitan fatty acid ester with ethylene oxide which forms a polymer having a molecular weight of 604.8 g/mol composed of PEG-ylated sorbitan. Its physical appearance is that of a yellow to orange colored, oily liquid. It is used as a surfactant, solubilizer, and emulsifying agent in multiple industries, including foods, soaps, and pharmaceuticals. Polysorbate is marketed under a variety of names including Monitan, Tween 80, Glycosperse, and polysorbate 80. Its IUPAC name is 2-[2-[3,4-bis(2-hydroxyethoxy)oxolan-2-yl]-2-(2-hydroxyethoxy)ethoxy]ethyl octadec-9-enoate. Polysorbate 80 has CAS Registry No. 9005-65-6. The chemical structure is provided in FIG. 1B.

Figure 1C:
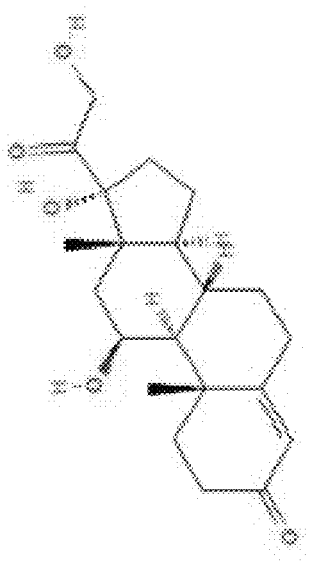

Hydrocortisone is a corticosteroid that exerts anti-inflammatory effects by binding to the glucocorticoid receptor. It has a molecular weight of 362.5 g/mol. It is also known as the human corticosteroid hormone cortisol produced by the adrenal cortex. Its physical appearance is that of a white crystalline powder. Hydrocortisone is marketed under a variety of names including Acticort, Cetacort, Dermacort, and Cortifan. Its IUPAC name is (8S,9S,10R,11S,13 S,14S,17R)-11,17-dihydroxy-17-(2-hydroxyacetyl)-10,13-dimethyl-2,6,7,8,9,11,12,14,15,16-decahydro-1H-cyclopenta[a]phenanthren-3-one. Hydrocortisone has CAS Registry No. 50-23-7. The chemical structure is provided in FIG. 1C.

Figure 1D:
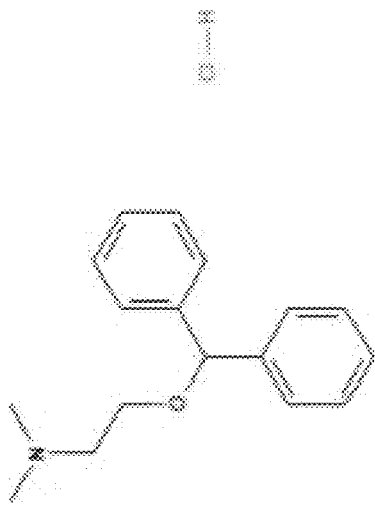

Diphenhydramine HCl is an antihistamine having a molecular weight of 291.8 g/mol. It is a histamine H1 receptor antagonist used to treat allergic reactions. Its physical appearance is that of a white or almost-white crystalline powder. Its more commonly known under its commercial name BENADRYL®. Its IUPAC name is 2-benzhydryloxy-N,N-dimethylethanamine; hydrochloride. Diphenhydramine HCl has CAS Registry No. 147-24-0. The chemical structure is provided in FIG. 1D.

Figure 1E:
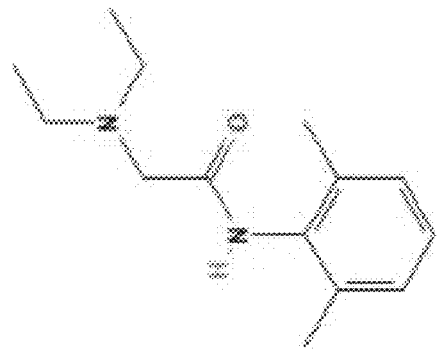
Figure 4:
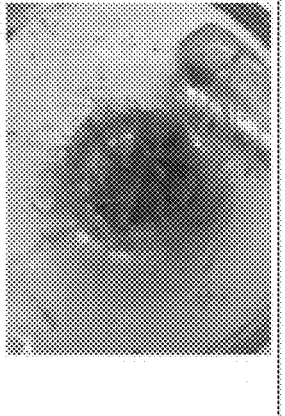

Lidocaine is a local anesthetic monocarboxylic acid amide resulting from the formal condensation of N,N-diethylglycine with 2,6-dimethylaniline. Names that lidocaine is marketed under include Lignocaine and Xylocaine. Its IUPAC name is 2-(diethylamino)-N-(2,6-dimethylphenyl)acetamide. Lidocaine acts by blocking sodium channels which inhibits nerves in local tissues from signaling pain. Lidocaine's molecular weight is 234.34 g/mol. Lidocaine appears as a white or slightly yellow, crystalline powder. Its IUPAC name is 2-(diethylamino)-N-(2,6-dimethylphenyl)acetamide. Lidocaine's CAS Registry No. is 137-58-6. The chemical structure is provided in FIG. 1E.

The ingredients of the composition can be formulated in various hydrophobic carriers such as creams, lotions, and ointment bases. According to some implementations, the composition is formulated in an ointment base having one or more ingredients chosen from petrolatum, mineral oil, and wax. While the hydrophobic carrier can vary in composition, two specific examples are provided below.

Petrolatum ointment base is a colloidal system of semisolid hydrocarbons derived from petroleum and used as an ointment base that is more commonly known as petroleum jelly and VASELINE®. Its physical appearance is that of a colorless, white, or yellowish to light amber semisolid or liquid. Petrolatum's CAS Registry Nos. are 8009-03-8, 8063-27-2, and 8027-32-5.

MEDISCA® Ointment Base (Emulsifying) is an anhydrous ointment base composed of mineral oil, white petrolatum, and emulsifying wax that can be used to prepare water-in-oil emulsions (Medisca Inc., Plattsburgh, NY, USA). It appears as a waxy, white to off-white ointment. It is sold under Product No. 0937.

Other ointment bases can also be used to formulate the composition, either as a component base ingredient with other base ingredients or as the entire base ingredient. A variety of hydrophobic and hydrophilic ointment bases are available. Hydrophobic bases are composed of hydrocarbons (oleaginous compounds) and include white ointment, white petroleum, mineral oil, wax and other paraffins, and VASELINE®. Hydrophilic bases include anhydrous absorption bases such as hydrophilic petrolatum, anhydrous lanolin, POLYSORB®, AQUAPHOR®, and AQUABASE®; these will absorb significant amounts of water. Water-in-oil emulsion ointment bases are hydrous bases such as hydrous lanolin, cold cream, EUCERIN®, HYDROCREAM®, rose water ointment, and NP/BA®. Other examples of hydrophilic absorption bases include oil-in-water emulsion bases, water-soluble bases, and gels. Formulas for these ointment bases have been described in the pharmacy literature (see De Villiers, Melgardt. (2009). Ointment Bases. In book: A Practical Guide to Contemporary Pharmacy Practice (pp. 277-290) Edition: 3 Chapter: 23 Publisher: Lippincott Williams & Wilkins Editors: Judith E Thompson; and Remington: The Science and Practice of Pharmacy (2020). Publisher: Academic Press, each incorporated herein by reference). The ointment bases can be chosen to incorporate the active pharmaceutical ingredients (APIs) of the composition, provide stability and consistency, and deliver them to the affected skin areas. Hydrophilic APIs such as povidone iodine in aqueous solution can be emulsified in the ointment base, such as an ointment base having one or more hydrophobic ointment base ingredients chosen from above, using methods of the disclosure, or otherwise incorporated as water-soluble ingredients if a hydrophilic ointment base is chosen.

More broadly, individual carrier ingredients in various combinations, representing hydrophobic and/or hydrophilic carrier substances, non-limiting examples including white petrolatum, white wax, mineral oil, vegetable oils, animal fats, mineral wax, beeswax, cholesterol, parabens, methylparaben, propylparaben, triethanolamine, propylene glycol, polyethylene glycol, wool wax alcohol, cetyl alcohol, stearyl alcohol, glycerol monostearate, isopropyl myristate, isopropyl palmitate, butyl stearate, and butyl palmitate, stearic acid, glycerin, cetyl esters wax, almond oil, rose oil, pine needle oil, purified water, rose water, carbomer 934, poloxamer 407, ethyl alcohol, isopropyl alcohol, high molecular weight alcohols, and branched chain fats or oils can be used to provide a base for formulating the inventive composition. The inventive composition of the disclosure preferentially incorporates one or more ingredients chosen from above that are hydrophobic or nonpolar as carrier substances, in combination with an emulsifier, as well as other ingredients such as stabilizers, penetration enhancers, antioxidants, pigments, or fragrances.

The ingredients can be formulated in the composition at the following concentrations:

BETADINE® (e.g., 5%, 7.5%, or 10% povidone iodine aqueous solution) can be included in the composition at a concentration of 0.1% to 20% (w/w), including 0.2%, 0.3%, 0.4%, 0.5%, 0.6%, 0.7%, 0.8%, 0.9%, 1.0%, 1.2%, 1.4%, 1.6%, 1.8%, 2%, 3%, 4%, 5%, 6%, 7%, 8%, 9%, 10%, 11%, 12%, 13%, 14%, 15%, 16%, 17%, 18%, and 19%, as well as values therebetween, as well as in any range encompassing these values such as 0.1% to 1%, 1% to 10%, 2% to 10%, 3% to 10%, 4% to 10%, 5% to 10%, 1% to 5%, 2% to 8%, 3% to 7%, 8% to 10%, 10% to 20%, 10% to 15%, 12% to 18%, 15% to 20%, 16% to 20%, 14% to 18%, 15% to 18%, 5% to 20%, 8% to 20%, 1% to 20%, 12% to 20%, 16% to 20%, and so on. In other implementations, BETADINE® concentrations exceeding 20% (w/w) including 21%, 22%, 23%, 24%, and 25%, or more, such as 30%, 35%, or 40%, are included in the composition.

In other implementations, the composition can incorporate generic forms of povidone iodine aqueous solution, instead of such solutions specifically marketed under the trade name BETADINE®. The composition can incorporate generic aqueous solutions of 1% to 20% povidone iodine, including 2%, 2.5%, 3%, 4%, 5%, 6%, 7%, 7.5%, 8%, 9%, 10%, 12%, 12.5%, 15%, 17.5%, and 20% povidone iodine as well as values therebetween, as well as in any range encompassing these values such as 5% to 10%, 2.5% to 10%, 2.5% to 12.5%, 5% to 17.5%, 7.5% to 12.5%, 7.5% to 15%, 15% to 20% povidone iodine, and so on, with an amount of povidone iodine aqueous solution incorporated in the composition in the range of a concentration of 0.1% to 20% (w/w), as recited above for BETADINE®. For example, the composition can be an ointment including 200 mg/gram (or 20% w/w) of a 10% povidone iodine solution, or 100 mg/gram (or 10% w/w) of a 10% povidone iodine solution, or 150 mg/gram (15% w/w) of a 10% povidone iodine solution, or including 200 mg/gram (or 20% w/w) of a 5% povidone iodine solution, or 100 mg/gram (or 10% w/w) of a 5% povidone iodine solution, or 150 mg/gram (15% w/w) of a 5% povidone iodine solution, or including 200 mg/gram (or 20% w/w) of a 20% povidone iodine solution, or 100 mg/gram (or 10% w/w) of a 20% povidone iodine solution, or 150 mg/gram (15% w/w) of a 20% povidone iodine solution, or including 200 mg/gram (or 20% w/w) of a 7.5% povidone iodine solution, or 100 mg/gram (or 10% w/w) of a 7.5% povidone iodine solution, or 150 mg/gram (15% w/w) of a 7.5% povidone iodine solution, or including 200 mg/gram (or 20% w/w) of a 15% povidone iodine solution, or 100 mg/gram (or 10% w/w) of a 15% povidone iodine solution, or 150 mg/gram (15% w/w) of a 15% povidone iodine solution, or the composition can be an ointment including 100-200 mg/gram (10-20% w/w) of a 5-10% povidone iodine solution. The generic povidone iodine aqueous solutions can be sourced from generic manufacturers or prepared directly from dry povidone iodine powder in an appropriate aqueous vehicle, such as sterile, distilled water.

Diphenhydramine HCL can be included in the composition at a concentration of 0.1% to 2% (w/w), including 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, and 1.9%, as well as values therebetween, as well as in any range encompassing these values such as 0.1% to 1.0%, 0.2% to 1.0%, 0.3% to 1.0%, 0.4% to 1.0%, 0.5% to 1.0%, 0.5% to 1.5%, 0.5% to 2.0%, 1.0% to 2.0%, 1.2% to 2.0%, 1.5% to 2.0%, 1.6% to 2.0%, 0.8% to 1.2%, 0.4% to 1.6%, 1.1% to 1.9%, and so on. In other implementations, diphenhydramine HCL concentrations exceeding 2% (w/w), including 2.1%, 2.2%, 2.3%, 2.4%, 2.5%, 2.6%, 2.7%, 2.8%, 2.9%, and 3.0%, or more, such as 3.5% or 4.0%, are included in the composition.

Hydrocortisone can be included in the composition at a concentration of 0.1% to 1.0% (w/w), including 0.2%, 0.3%, 0.4%, 0.5%, 0.6%, 0.7%, 0.8%, and 0.9%, as well as values therebetween, as well as in any range encompassing these values, including 0.1% to 1.0%, 0.2% to 1.0%, 0.3% to 1.0%, 0.4% to 1.0%, 0.5% to 1.0%, 0.6% to 1.0%, 0.2% to 0.8%%, 0.4% to 0.8%, 0.5% to 0.8%, 0.1% to 0.9%, 0.5% to 0.9%, 0.3% to 0.9%, 0.6% to 0.9%, and so on. In other implementations, hydrocortisone concentrations exceeding 1.0% (w/w), including 1.1%, 1.2%, 1.3%, 1.4%, and 1.5%, or more, such as 1.6%, 1.7%, 1.8%, 1.9%, or 2.0%, are included in the composition.

Lidocaine can be included in the composition at a concentration of 0.1% to 4.0% (w/w), including 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, as well as values therebetween, as well as in any range encompassing these values, such as 1.0% to 4.0%, 0.5% to 4.0%, 1.5% to 4.0%, 2.0% to 4.0%, 2.5% to 4.0%, 3.0% to 4.0%, 1.0% to 3.0%, 1.5% to 3.5%, 1.2% to 3.8%, 0.5% to 3.5%, 1.4% to 3.8%, 0.5% to 3.9%, 2.2% to 4.0%, and so on. In other implementations, lidocaine concentrations exceeding 4.0% (w/w), including 4.1%, 4.2%, 4.3%, 4.4%, 4.5%, 4.6%, 4.7%, 4.8%, 4.9%, and 5.0%, or more, such as 6%, 7%, or 8%, are included in the composition.

Polysorbate 80 can be included in the composition at a concentration of 0.1% to 8.0% (w/w), including 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 3.0%, 4.0%, 5.0%, 6.0%, 7.0%, as well as values therebetween, as well as any range encompassing these values, including 2.0% to 4.0%, 2.0% to 6.0%, 3.0% to 5.0%, 6.0% to 8.0%, 4.0%, to 8.0%, 5.0% to 8.0%, 5.0% to 7.0%, 3.0% to 6.0%, and 2.0% to 8.0%. In other implementations, polysorbate 80 concentrations exceeding 8.0% (w/w), including 8.2%, 8.4%, 8.6%, 8.8%, 9.0%, 9.5%, 10.0%, 10.5%, 11.0%, and 12.0%, or more, such as 13%, 14%, 15%, or 16%, are included in the composition.

The ingredients can be formulated as an emulsion using an oleaginous ointment base (e.g., petrolatum), a water-in-oil emulsifying ointment base (e.g., MEDISCA® Emulsifying Ointment Base), or a combination thereof. The ingredients can also be formulated in other hydrophobic carriers such as other ointments, lotions, and creams. In other implementations, the ingredients are formulated in pastes, gels, or impregnated substances. The ingredients can be formulated by weighing out an appropriate amount of each ingredient to achieve a desired concentration and mixing using a mortar and pestle or mechanical pharmaceutical mixer or blender until a homogenous composition is achieved. For example, in one implementation, a povidone iodine aqueous solution is first added to a hydrophobic carrier at a desired concentration, and then an appropriate amount of emulsifier such as polysorbate 80 is gradually and incrementally added and mixed into the hydrophobic carrier until the aqueous solution of povidone iodine is entirely emulsified in the hydrophobic carrier. Example 4 illustrates an ingredient list with appropriate weights for compounding, to achieve one particular embodiment of the inventive composition.

The inventive compositions are useful for treating inflammatory skin conditions and rashes including bites and stings, infections, autoimmune diseases, and allergies. Examples of inflammatory skin conditions that can be treated include insect bites or stings, such as those from mosquitos, flies (e.g., horseflies, blackflies, deerflies, sandflies), bees, yellowjackets, hornets, spiders, scorpions, ants, wasps, fleas, ticks, chiggers, lice, scabies, kissing bugs, and bed bugs. Other examples include bites or scratches from animals including rodents, cats, dogs, and reptiles. Other examples include rashes from contact with poisonous plants, such as poison oak, poison ivy, poison sumac, and stinging nettle. Other examples include drug rashes, such as those produced by systemic allergic reactions to medications such as antibiotics, allopurinol, anti-epileptic drugs, nonsteroidal anti-inflammatory drugs (NSAIDs), and vaccines. Other examples include direct contact dermatitis resulting from topical exposures from certain substances such as antibiotics, antiseptics, preservatives, rubber products, detergents, or metals. Other examples include viral skin infections such as herpes simplex virus 1 and 2 or herpes zoster. Other examples include fungal skin infections, such as tinea pedis and tinea versicolor. Other examples include autoimmune conditions such as psoriasis. These are merely illustrative examples, and more will be apparent to the skilled artisan. The inflammatory skin condition can present as rashes (e.g., erythema multiforme, erythema nodosum), hives, welts, blisters, areas of itching, and/or combinations thereof. An appropriate amount of the composition (e.g., 0.1 grams to 5 grams) can be applied dermally at the site of the inflammatory skin condition until symptoms of the inflammatory dermal condition such as pruritis, pain, swelling, and redness are reduced or eliminated, such as applied for 1 minute, 2 minutes, 3 minutes 4 minutes, 5 minutes, 6 minutes, 7 minutes, 8 minutes, 9 minutes, 10 minutes, 12 minutes, 15 minutes, 20 minutes, 25 minutes, 30 minutes, 45 minutes, 60 minutes, or longer.

Examples 1-3 below describe experiments undertaken to determine the correct ingredients and amounts of ingredients for the inventive compositions that provide an ointment with appropriate homogeneity, consistency, stability, and other material properties for medical applications for treating inflammatory skin conditions. The experiments also determined an appropriate emulsifying agent and concentration of the emulsifying agent for formulating BETADINE® (10% povidone iodine aqueous solution), which is water-soluble, into a fat-soluble ointment base. Example 1 describes experiments testing the effectiveness of three different emulsifiers (polysorbate 80, sorbitan monooleate, polysorbate 20) on the consistency of a 20% (w/w) BETA-DINE® ointment in an emulsifying base. Example 2 describes experiments testing the effectiveness of two different concentrations of polysorbate 80 (4% w/w and 8% w/w) and two different ointment bases on the consistency of a 20% BETADINE® ointment. Example 3 provides results of experiments testing different implementations of ointments with fixed amounts of polysorbate 80, hydrocortisone, and diphenhydramine and different concentrations of BETADINE® (10% w/w, 15% w/w, 20% w/w) using different ointment bases. Example 4 describes one particular embodiment of the inventive compositions.

Figure 6:
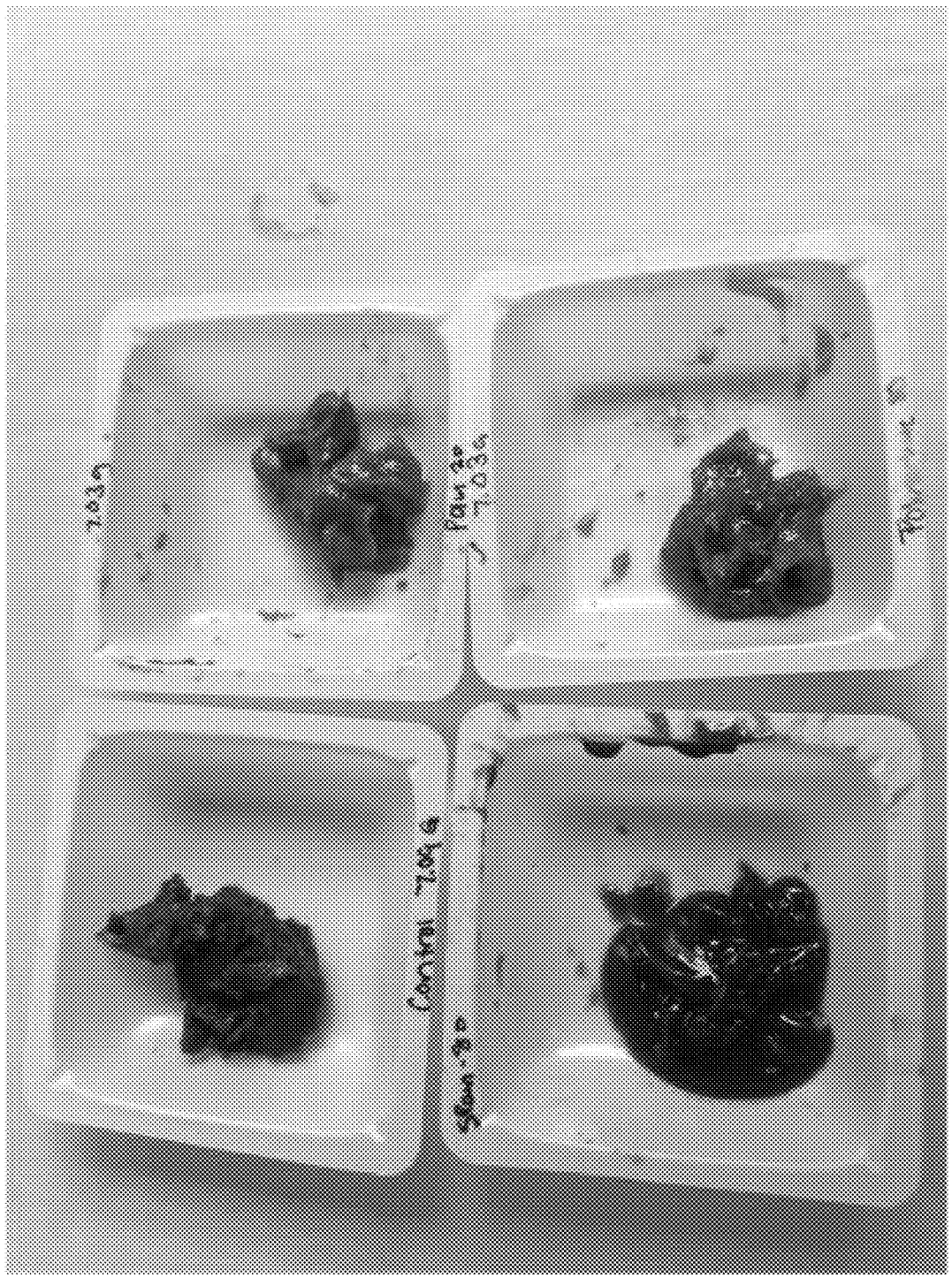
FIG. 6 is an image showing the resulting formulations of the experiments of FIGS. 2-5 (control-top left, polysorbate 20-top right, sorbitan monooleate-bottom left, and polysorbate 80-bottom right).

Example 1: 20% BETADINE® Ointment in Emulsifying Base; Experiment with Three Different Emulsifiers FIGS. 2-5 are tables showing the results of ointment formulation experiments of a 20% w/w BETADIINE® ointment in MEDISCA® Emulsifying Base testing three different emulsifiers (polysorbate 80, sorbitan monooleate, polysorbate 20). FIG. 6 is an image showing the resulting formulations (control-top left, polysorbate 20-top right, sorbitan monooleate-bottom left, and polysorbate 80-bottom right). The experimental protocol is provided below.

Figure 7:
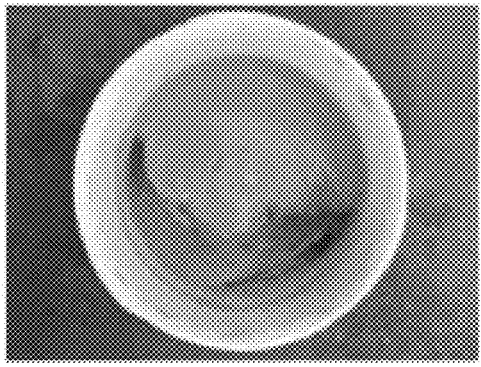
FIG. 7 is a table showing the results of an ointment formulation experiment comparing formulations of 20% BETADINE® using different bases (MEDISCA® Emulsifying Ointment Base or petrolatum white) and, for petrolatum white, two different concentrations of emulsifier (polysorbate 80 4% w/w vs. polysorbate 80 8% w/w).

Base. MEDISCA® Emulsifying Ointment Base
Materials:
1. 3 glass mortar and pestle
2. Existing 20% BETADINE® w/w ointment
3. Emulsifiers
   polysorbate 80, NF
   sorbitan monooleate (Span 80)
   polysorbate 20 NF
4. 3 syringes
Procedure:
1. Gather compound and try to mend together first in aliquoted amounts.
2. Weigh compound then divide weight by 4 (control and 3 test emulsifiers) each weighing 7 g. Total weight is 28 g. Record weight of each below:
   Weight of Control: _____ 7.09 g _____
3. Place ¼ of compound into corresponding mortar and pestle. One emulsifier per mortar and pestle.
4. Drop one drop (0.1 mL) of 1st emulsifier and write a description of consistency (image is acceptable).
   a. Draw up 0.1 mL with a syringe and wipe before placing on a scale to measure.
   b. Measure syringe with emulsifier.
   c. Inject 0.1 mL into mortar with compound.
   d. Measure empty syringe.
   e. Blend 1st emulsifier with compound.
5. Continue until consistent (estimated amounts to consistent 0.5-6%~0.3 mL)
6. Repeat steps 4-5 with other emulsifiers.
Beaker 28.85 grams
Syringe 2.61 grams Example 2: 20% BETADINE® Ointment Base, Polysorbate 80 Concentration Comparison Experiment FIG. 7 is a table showing the results of an ointment formulation experiment comparing ointment formulations of 20% w/w BETADIINE® using different bases (MEDISCA® Emulsifying Ointment Base or petrolatum white) and, for petrolatum white, two different concentrations of emulsifier (polysorbate 80 4% w/w vs. polysorbate 80 8% w/w). The experimental protocol is provided below.

Figure 9:
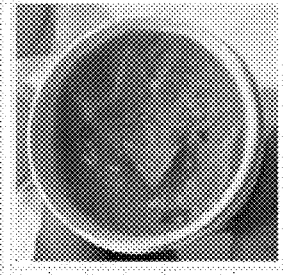

Materials:
Base: MEDISCA® Emulsifying Ointment Base or petrolatum white
Emulsifier: polysorbate 80 Active Pharmaceutical Ingredient (API): BETADINE®
Procedure:
1. Place an empty (emp) jar onto a scale and zero out its weight.
2. Weigh out 14.4 g of emulsifying base into the emp jar. Record actual weight.
    a. Base (emulsifying ointment): _____14.446 g_____
3. Zero out emp jar with base. Add 4 g of BETADINE® into the zeroed jar already containing base. Record actual weight:
    a. API (BETADINE®): _____4.01 g_____
4. Zero the emp jar containing base and API for one last time.
5. Using a syringe, measure out 1.6 g (~1.6 ml) of polysorbate 80. This will be the last ingredient to add to the emp jar. Record actual weight.
    a. Polysorbate 80: _____1.6 g_____
6. Take the emp jar containing all ingredients to be mixed. Settings:
    a. Speed: 2
    b. Time: 1 minute
7. Remove jar from mixer and record description of compound.
8. Repeat steps 1-7 with base as petrolatum. Record weights each step.
    a. Base (petrolatum): 14.41 g
    b. API (BETADINE®): 4.02 g
    c. Polysorbate 80: 1.61 g
9. Repeat steps 1-7 with Polysorbate 80 (0.8 g), petrolatum 15.2 g, API 4 g. Record weights.
    a. Base (petrolatum): 15.23 g
    b. API (BETADINE®): 4.01 g
    c. Polysorbate 80: 0.83 g Example 3: Ointment Formulation Experiments with Different Concentrations of BETADINE® and Different Bases FIGS. 8 and 9 are tables showing summaries of ointment formulation experiments using different concentrations (10%, 15%, 20% w/w) of BETADINE® in petrolatum (FIG. 8), and 20% w/w BETADINE® in different bases (emulsifying base, 50% emulsifying base/50% petrolatum, 25% emulsifying base/75% petrolatum, FIG. 9). The ointment formulations include fixed amounts of polysorbate 80 (8% w/w), hydrocortisone (1% w/w), and diphenhydramine (2% w/w). The tables list each of the ingredients, concentrations, and calculated and actual weights and an image of the resulting ointment taken after compounding.

Figures 10A, 10B:
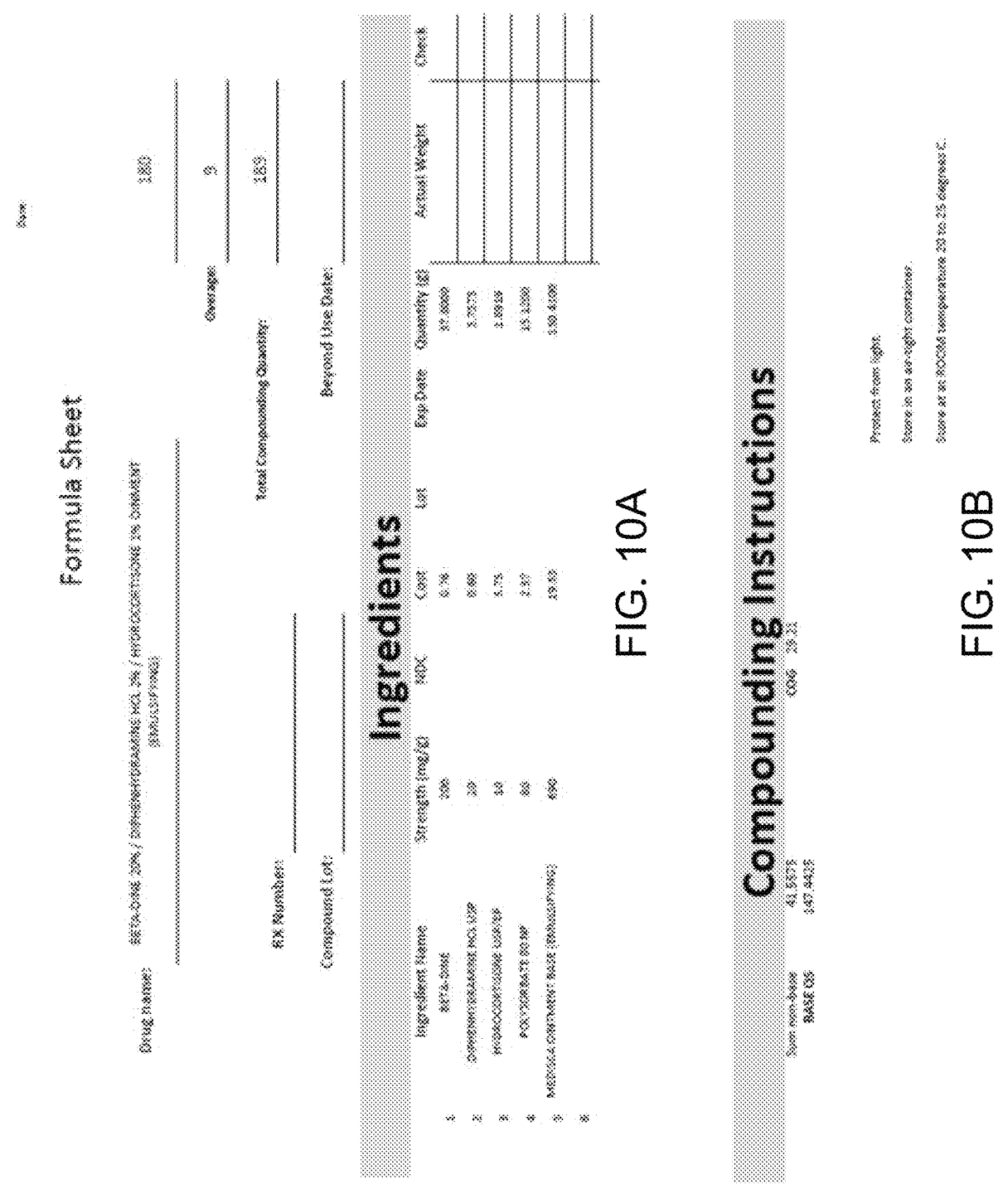

Example 4: Formula of a BETADINE® 20%/Diphenhydramine HCl 2%/Hydrocortisone 1% Ointment (Emulsifying) for Compounding FIG. 10A is a formula sheet showing an example ointment formulation ingredient list. The ingredient list is for an ointment having 20% w/w BETADINE® (10% povidone iodine aqueous solution), 2% w/w diphenhydramine HCL, 1% w/w hydrocortisone, and 8% w/w polysorbate 80, compounded in a MEDISCA® Emulsifying Ointment Base. FIG. 10B is an image providing instructions for compounding the ingredients listed in FIG. 10A.

The present disclosure has described particular implementations having various features. In light of the disclosure provided above, it will be apparent to those skilled in the art that various modifications and variations can be made without departing from the scope or spirit of the disclosure. One skilled in the art will recognize that the disclosed features may be used singularly, in any combination, or omitted based on the requirements and specifications of a given application or design. When an implementation refers to "comprising" certain features, it is to be understood that the implementations can alternatively "consist of" or "consist essentially of" any one or more of the features. Other implementations will be apparent to those skilled in the art from consideration of the specification and practice of the disclosure.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the disclosure fall within the scope of the disclosure. Further, all of the references cited in this disclosure including patents, published applications, and non-patent literature are each individually incorporated by reference herein in their entireties and as such are intended to provide an efficient way of supplementing the enabling disclosure as well as provide background detailing the level of ordinary skill in the art.

The invention claimed is:
1. A composition, comprising:
povidone iodine aqueous solution;
hydrocortisone;
diphenhydramine;
polysorbate 80; and
a hydrophobic carrier;
wherein the povidone iodine aqueous solution is emulsified in the hydrophobic carrier by the polysorbate 80;
wherein the composition is effective in eradicating insect bite immune response sequela when applied to skin.
2. The composition of claim 1, further comprising lidocaine.
3. The composition of claim 1, wherein the hydrophobic carrier is a cream, lotion, or ointment.
4. The composition of claim 1, wherein:
the povidone iodine aqueous solution is present in the composition at a concentration of 0.1% to 20% (w/w);
hydrocortisone is present in the composition at a concentration of 0.1% to 1.0% (w/w);
diphenhydramine is present in the composition at a concentration of 0.1% to 2% (w/w); and
polysorbate 80 is present in the composition at a concentration of 0.1% to 8.0% (w/w).
5. The composition of claim 1, wherein:
the povidone iodine aqueous solution is present in the composition at a concentration of 20% (w/w);
hydrocortisone is present in the composition at a concentration of 1% (w/w);
diphenhydramine is present in the composition at a concentration of 2% (w/w); and
polysorbate 80 is present in the composition at a concentration of 8% (w/w).

6. The composition of claim 1, wherein the:
- the povidone iodine aqueous solution is present in the composition at a concentration exceeding 20% (w/w); or
- hydrocortisone is present in the composition at a concentration exceeding 1% (w/w); or
- diphenhydramine is present in the composition at a concentration exceeding 2% (w/w); or
- polysorbate 80 is present in the composition at a concentration exceeding 8% (w/w).

7. The composition of claim 1, wherein the hydrophobic carrier is an anhydrous ointment base comprising mineral oil, white petrolatum, and emulsifying wax and is capable of preparing water-in-oil emulsions.

8. The composition of claim 1, wherein the hydrophobic carrier comprises petrolatum.

9. The composition of claim 4, wherein the hydrophobic carrier is an anhydrous ointment base comprising mineral oil, white petrolatum, and emulsifying wax and is capable of preparing water-in-oil emulsions.

10. The composition of claim 4, wherein the hydrophobic carrier comprises petrolatum.

11. The composition of claim 2, wherein lidocaine is present in the composition at a concentration of 0.1% to 4.0%.

12. The composition of claim 2, wherein lidocaine is present in the composition at a concentration of 4.0%.

13. The composition of claim 2, wherein lidocaine is present in the composition at a concentration exceeding 4.0%.

14. A method of preparing a composition, comprising:
- adding a povidone iodine aqueous solution to a hydrophobic carrier; and
- adding polysorbate 80 to the hydrophobic carrier at a concentration that emulsifies the aqueous solution of povidone iodine in the hydrophobic carrier upon mixing;
- adding hydrocortisone, diphenhydramine, and optionally lidocaine, wherein the composition is effective in eradicating insect bite immune response sequela when applied to skin.

15. The method of claim 14, wherein the povidone iodine aqueous solution is added at a concentration of 0.1% to 20% (w/w) and polysorbate 80 is added at a concentrations of 0.1% to 8.0% (w/w).

16. The method of claim 14, wherein the povidone iodine aqueous solution is added at a concentration of 20% (w/w) and polysorbate 80 is added at a concentration of 8.0% (w/w).

17. The method of claim 14, wherein the hydrophobic carrier is an anhydrous ointment base comprising mineral oil, white petrolatum, and emulsifying wax and is capable of preparing water-in-oil emulsions.

18. The method of claim 14, wherein the hydrophobic carrier comprises petrolatum.

* * * * *